(12) United States Patent
Horino et al.

(10) Patent No.: US 6,416,573 B2
(45) Date of Patent: Jul. 9, 2002

(54) COMPOSITE PIGMENT AND COSMETICS CONTAINING THE SAME

(75) Inventors: Masaakira Horino, Kanagawa; Miwa Nishizawa, Saitama, both of (JP)

(73) Assignee: Miyoshi Kasei, Inc., Saitama (JP)

( * ) Notice: Subject to any disclaimer, the term of this patent is extended or adjusted under 35 U.S.C. 154(b) by 0 days.

(21) Appl. No.: 09/778,875

(22) Filed: Feb. 8, 2001

(30) Foreign Application Priority Data

Feb. 14, 2000 (JP) .......................................... 2000-034766
Sep. 1, 2000 (JP) .......................................... 2000-265026

(51) Int. Cl.$^7$ .............................................. C04B 14/04
(52) U.S. Cl. .................... 106/486; 428/403; 424/78.03; 514/844
(58) Field of Search .................... 106/486; 428/403; 424/401, 682, 684, 78.03; 514/844

(56) References Cited

U.S. PATENT DOCUMENTS

| | | | |
|---|---|---|---|
| 4,040,859 A | * | 8/1977 | Esselborn et al. |
| 4,045,235 A | * | 8/1977 | Bidwell et al. |
| 4,084,983 A | * | 4/1978 | Bernhard et al. |
| 4,450,012 A | * | 5/1984 | Messer et al. |
| 4,490,179 A | * | 12/1984 | Bernhard |
| 4,545,821 A | * | 10/1985 | Rau et al. |
| 4,952,245 A | * | 8/1990 | Iwano et al. |
| 5,792,250 A | * | 8/1998 | Braun et al. |

FOREIGN PATENT DOCUMENTS

| | | | |
|---|---|---|---|
| JP | 50004021 | * | 2/1975 |
| JP | 59-36160 | | 2/1984 |
| JP | 61-56258 | | 3/1986 |
| JP | 7-2619 | | 1/1995 |
| JP | 9-20609 | | 1/1997 |
| JP | 9-48716 | | 2/1997 |

* cited by examiner

Primary Examiner—Paul Marcantoni
(74) Attorney, Agent, or Firm—Armstrong, Westerman & Hattori, LLP

(57) ABSTRACT

There is provided a composite pigment comprising a clay mineral and an aluminum hydroxide that adheres to the surface of said clay mineral, wherein said aluminum hydroxide contains an aluminum hydroxide in the form of a cup with cover, the basal plane of which adheres to the surface of said clay mineral, and preferably contains such specified aluminum hydroxide as much as possible, which shows excellent transparency, makes both the troubled morphology of the skin such as, wrinkles, pore openings, hard texture of the skin less noticeable, and the trouble color tone of the skin such as, blemishes, freckles, and acne traces less noticeable, when included in cosmetics, as well as having a smoother feel and lesser color drabness, and makes the skin look brighter, when compared to conventional products.

When an aluminum hydroxide layer is covered on the said composite pigment, or a silicone surface treatment is placed on the said composite pigment, the above-defined purpose of the present invention can be increased to an even higher extent.

17 Claims, 4 Drawing Sheets

(×15,000)

(×15,000)

(×50,000)

(×10,000)

(×5,000)

COMPOSITE PIGMENT AND COSMETICS CONTAINING THE SAME

BACKGROUND OF THE INVENTION

1. Field of the Invention

The present invention relates to a novel composite pigment, which comprises an aluminum hydroxide-clay mineral composite particle; in which said aluminum hydroxide of a specific structure adheres to the particle surface of said clay mineral. Furthermore, this invention relates to a composite pigment, that remarkably hides the troubled morphology of the skin, such as wrinkles, pore openings, hard texture of the skin, and at the same time, remarkably hides the troubled color tone of the skin, such as blemishes, freckles, and acne traces and the like, and compared to conventional products, has a smoother finish on the skin and has less color drabness, and is much more transparent and therefore makes the skin look brighter, when used for the cosmetics, and also relates to cosmetics, which contain the same.

2. Description of the Related Art

Until now, there were many types of make-up formulations that contained high concentrations of titanium dioxide, which had high covering power, because of its opaqueness, in order to hide the troubled color tone of the skin, such as blemishes, freckles, and acne traces on the skin. These types of make-ups have some effect on hiding the troubled color tone of the skin, but usually have a completely reversed effect on hiding the troubled morphology of the skin. Generally, it is thought that by hiding the troubled color tone of the skin, the troubled morphology of the skin is also hidden. However, there are overwhelmingly many cases, where when only covering power is used, the troubled morphology is not only unhidden, but actually makes the troubled morphology stand out. From such facts, research has begun on ways to hide the troubled skin morphology, aside from using high covering power.

In the Japanese Patent Kokai Publication JP-A-61-69708, extender pigments for cosmetics, such as talc, kaolin, mica, sericite and the like surface treated with acrylic resin has been proposed, but when the acrylic resin surface treatment on the extender pigment increased beyond 5%, the feeling worsened, and a discomfort (pain) occurred on the skin, which made its use, at levels that show some effect, very difficult. When used in large quantities in dry powder formulations, troubled skin morphology is hidden to some extent, however, this composite pigment has a defect of blurring the contour of the face, because the powder scatters diffused light from its surface, making the face look larger. Also, composites of this type have a defect of making blemishes stand out. In addition, when it gets wet by sebum and perspiration secreted by the skin, it becomes completely transparent, thereby negating the hiding effect of the troubled skin morphology.

In the Japanese Patent Kokai Publication JP-A-7-2619, mica powder, which has excellent feel and pressability (formability), and can substitute for sericite with small luster suitable for cosmetics, is proposed. However, the reflection pattern of light of this mica powder is greatly different from that of the skin surface, and therefore does not create any skin-like texture, producing a makeup that does not simulate the skin. In addition, a reflection pattern is produced, which is similar to a specular reflection, creating an unnatural gloss, and makes wrinkles stand out.

In the Japanese Patent Kokai Publication JP-A-59-36160, talc, which has the talc surface covered with metal hydroxide, has been proposed. It is shown in this document that, the talc particle has improved hydrophobicity on its surface, and has good dispersive properties as an extender pigment, and when different types of water-soluble metal compounds are used, colored talc pigment with colored pigment properties, such as black, red, yellow, blue, orange, etc., with good dispersive properties may be processed. However, the following have not completely been shown: The hiding effect of troubled morphology of the skin, and hiding effect of the troubled color tone, smooth feeling and small color drabness, high transparency, and an effect of making the skin look brighter. And, by viewing the practical example of this document, the results of the hiding effect of the troubled morphology of the skin and troubled skin tone, show data that is not acceptable in terms of our purpose of this invention.

In the Japanese Patent Kokai Publication JP-A-61-56258, talc and sintered talc that is uniformly and perfectly covered on all surfaces of the talc particle, by a metal hydroxide and/or a composition which consists only of a metal oxide, can be processed to any desired color, and has excellent pigment properties, such as dispersiveness, is proposed. However, the following have not completely been shown: The hiding effect of troubled morphology of the skin and troubled color tone, and also smooth feeling and small color drabness, high transparency, and an effect of making the skin look brighter. And, by viewing the practical example of this document, the results of the hiding effect of the troubled morphology of the skin and troubled skin tone, show data that is not acceptable in terms of our purpose of this invention as was shown above.

In addition, in Japanese Patent Kokai Publication JP-A-9-20609, a surface treated powder (the composite pigment) with the covered structure of the inorganic metal hydroxide, which covers the surface of a clay mineral contained in cosmetics, given by the following (A), (B), (C) or (D), is proposed.

(A) A complex, which has a honeycomb structure, on top of a film of inorganic metal hydroxide that covers the surface of a clay mineral, formed with ultrafine particles (average particle size of 50~250 Å).

(B) A complex, which has a film of inorganic metal hydroxide that covers the surface of a clay mineral, formed with ultrafine particles (average particle size of 50~250 Å).

(C) A complex, which has a film of inorganic metal hydroxide that covers the surface of a clay mineral, formed with ultrafine particles (average particle size of 50~250 Å), and a honeycomb structure, intermingled within a film surface.

(D) A complex, which has particles of average particle size 0.08~0.8 μm, embedded within the film of inorganic metal hydroxide of ultrafine particles with an average particle size of 50~250 Å, that covers the surface of the clay mineral.

When this composite pigment, has its honeycomb structure on its external layer, the said structure makes the pigment have good adhesion to the skin, because of its ability to entangle with the corrugated surface of the skin, but the honeycomb structure will inversely destroy the good feeling, which is generally required, of cosmetics. Also, a complex, which has its external layer similarly covered with ultrafine particles, will have a heavy drag and bad extension on the skin, generally associated with ultrafine particles themselves, and when used in quantities of over 5 weight % in cosmetics, will drastically put a burden on the skin, and thereby make it difficult to use in cosmetics in sufficient large concentrations.

Over the past several years, sericite with good qualities have become exhausted, and there seems to be a strong demand for a material that can substitute for sericite. There has been some material development on holding the luster of mica, by applying friction to the surface of mica and making the surface corrugated, but this in turn makes the mica have a heavy drag on the skin, and the stability of the degree of luster, is very wide and its control becomes very difficult. In addition, when the mica surface is wetted by sebum and perspiration that is secreted by the skin over time, the grayish-brown color that is representative of mica becomes emphasized, and the desired makeup effect cannot be obtained. Also, when the sebum and perspiration that the skin secretes in excess covers and overlays the said ultrafine corrugated surface, the gloss becomes emphasized, and defects such as wrinkles stand out.

Makeups generally require different cosmetic effective luster, in order to correspond to various changes in texture. For this reason, clay minerals with good smoothness of the surface, such as talc, sericite, and mica are generally used with white extender pigments such as silica powders, calcium carbonate, and magnesium carbonate, or spherical pigments in different combinations are selected in formulations in order to adjust the total luster of the entire cosmetic.

However, when the cosmetic is applied to the skin, since the surface of the clay mineral is very smooth, the cosmetic film that it produces on the skin becomes shiny, thereby, becoming the reason why the troubled morphology of the skin becomes emphasized. In order to overcome this problem, it is necessary to lower the level of inclusion of clay minerals that has smooth surfaces. As a result, the benefits of clay minerals with smooth surfaces, such as transparency, smoothness when extended on the skin, adhesion to the skin can not be sufficiently brought about, creating additional problems.

The refractive index of oil solutions that are usually used in cosmetics is 1.39~1.51, while the refractive index of mica is 1.59 and talc is 1.53, which represents clay minerals that are often used in cosmetics, while the refractive index of the stratum corneum is 1.55. As can be seen from the numbers above, when normal pigments are used in cosmetics, the refractive index is very similar to each other, and when the pigments are wetted with skin secreted sebum at its oil absorption or over this amount, the pigments that make up the said cosmetic film on the skin, become transparent. When an excess amount of sebum is secreted, a reflection from the surface of the sebum film, as well as the reflection from the surface of the clay minerals dispersed within the sebum, will emphasize and create an undesirable shine, that when viewed from different angles will make the wrinkles stand out, and in occasion make the wearer of the cosmetic have a very tired look.

In order to prevent these shines, materials with high oil absorption are used, such as porous acrylic beads, titanium dioxide trapped in porous acrylic beads, porous silica, aerosils, magnesium carbonate, etc. However, when makeups, which contain these materials, are applied to the skin, the skin becomes very dry and parched, and a feeling of discomfort arises.

Fluorine treated powders are lipophobic, and so normal oil coating methods used in the production of compact cosmetics will negate this property. However, there are cosmetics that do contain fluorine treated powders, which are used as anti-shine material, but perspiration and sebum which the skin secretes for example, will in this case find its way to the top of the cosmetic film on the skin, and create a shine over time. Therefore, there are too many problems to overcome, in order to use this type of material efficiently.

In order to create a beautiful makeup film on the skin, and from a viewpoint of raising the cosmetic effect, a control color is used as a base, beneath the foundation itself. Some of the main color tones used are green, yellow, purple, orange, etc. The aim of these color tones are to remove the redness of the skin (utilization of the complementary color relation with the redness of the skin), make the color of the skin brighter and more natural, and make the skin look healthier by using effective colors. In order to make blemishes and freckles less noticeable, if for example, a color tone of the blemish is used in a cosmetic, the cosmetic film becomes very dark, and a desirable cosmetic effect becomes very difficult. In order to make blemishes less noticeable, it is better to use green. However, in this case, the chroma of the foundation color tone becomes low, because of decreased color mixing effect, which occurs when the control colors mix with the foundation, and the original color effect of the foundation is greatly reduced. In addition, the steps associated with putting on the cosmetic becomes very complicated, because the amount that is supposed to be used becomes very precise, that a very advanced technique becomes necessary, if the user wants a good cosmetic effect.

SUMMARY OF THE INVENTION

1. Problem to be Solved by the Invention

Based on the above defined facts, a powder, when used in cosmetics that imparts excellent transparency, hides the troubled morphology of the skin such as wrinkles, pore openings, hard texture of the skin, and at the same time, hides the troubled color tone of the skin, such as blemishes, freckles, and acne traces, and imparts a smooth feeling, as well as having very low color drabness, and makes the skin look brighter, is desired.

The purpose of the present invention, is to improve upon the previous document of Japanese Patent Kokai Publication JP-A-9-20609, also written by the same present inventors, and propose a powder, which further augments the hiding of troubled morphology of the skin and troubled skin tone color, and which especially has a good feel (smoothness) when used in cosmetics, along with less color drabness, and makes the skin look brighter.

2. Detailed Description of the Invention

After diligent research on the aforementioned problem, the present inventors have come up with an invention that is a powder, which comprises of a composite powder of clay minerals, where the surface of the clay minerals comprises of specific structured particles of aluminum hydroxide (particle, and multiple particles) adhered onto it. When said composite particle is used in cosmetics, it imparts high transparency, hides both the troubled morphology of the skin and troubled skin tone color, as well as imparting a smooth feel and low color drabness, and makes the skin color look brighter. Furthermore, upon adding a layer of aluminum hydroxide, especially of ultrafine particles, onto the surface, or adding a silicone surface treatment layer, the above-defined properties are increased to an even higher effect, thereby completing this invention.

In this invention, a composite pigment, where a clay mineral, and particularly said clay mineral that contains an aluminum hydroxide adhered on its said surface is contained, where the adhered aluminum hydroxide constitutes a specific structure, where the particle of the clay mineral is specific, for example specific size, thickness, and refractive index, and which at least contains an aluminum hydroxide that has a specific structure and adheres to the surface of said clay mineral, and has a suitable refractive index (1.56) and density (2.77g/cm$^3$), and when used in cosmetics will impart an excellent effect that was not previously possible, and which may be called particle (composite pigment) that includes this complex particle, is offered.

That is to say, the present invention is as follows.

[1] A composite pigment (powder) comprising a clay mineral (powder composed of a clay mineral particle, etc.) and an aluminum hydroxide that adheres to the surface of said clay mineral, wherein said aluminum hydroxide contains an aluminum hydroxide (as an edifice or structure of the aluminum hydroxide particle) in the form of a cup with cover, the basal plane of which adheres to the surface of said clay mineral, which can be used in cosmetics. In such case, the clay mineral that has many cup-like structures on said surface is more preferable.

In addition, if it does not inhibit the purpose and effect of this invention, any other components (substrate powder components, adhered particle compositions, etc.) may be included in the composite pigment of the present invention, and any other surface treatments maybe performed, and any other material that may be used to cover the above-defined product may be present thereon. They are all included in this invention.

While it is also possible to use this composite pigment in cosmetics, it is also possible to use in various other products, such as inks, paints and varnishes and the like, and other pigments.

[2] The composite pigment as defined above, wherein said aluminum hydroxide, where the adhered aluminum hydroxide particle constitutes a cup-like structure with a cover, contains an aluminum hydroxide, where the top surface of the cover is somewhat (approximately) parallel to the cup basal plane, or has a somewhat (approximately) muffin-like structure, where the top cover has a curved surface that swells outward.

The lateral face (side surface) part of the cup in said cup-like structure thereof may have one, where the cross section in the horizontal direction (lateral cross section) of the cup-like structure may impart a somewhat circular, a somewhat elliptical shape, or a somewhat polygon (quadrangle, etc.) shape, which has some of its parts that juts outside. In addition, in the case of a structure which has several edges, it is more desirable that the cup-like structure have a curved surface shape in which the corners formed (two edges in case of a cross-sectional), such as in a polygonal case, have a roundness, and it is possible to also include these curved surface shapes in the lateral cross sectional polygon shapes as well, in the present invention.

This invention seems to obtain its excellent feel (smoothness, etc.), from the fact that the top surface of the cover of the cup-like structure has a smooth planar shape or has a gentle curved shape (muffin-like structure), thereby obtaining the desired purpose.

In this invention, the terminology of "approximately" and "somewhat" is used abundantly in the entire description, and it is meant that this may perfectly have such a structure, or that the structure may be similar to the stated structure, and that it is alike. Therefore, the term "somewhat parallel" or "almost parallel" can mean both a completely parallel, and a somewhat parallel condition. And, the term "somewhat circular" can mean those that are completely circular, those that are somewhat circular, and shapes that are cylindrical, and those that are somewhat cylindrical, and they are all included therein.

[3] The composite pigment as defined above, wherein said clay mineral has particles with an average particle size of approximately 0.2~50 μm, and more suitably approximately 0.3~30 μm, and even more suitably approximately 2~15 μm, or contains particles with a particle size of approximately 0.2~50 μm, and more suitably approximately 0.3~30 μm, and even more suitably approximately 2~15 μm.

[4] The composite pigment as defined above, wherein said clay mineral has particles with an average thickness of approximately 0.05~1.5 μm, and more suitably approximately 0.2~1.0 μm, or contains particles with a thickness of approximately 0.05~1.5μm, and more suitably approximately 0.2~1.0 μm.

[5] The composite pigment as defined above, wherein the substances in the said form of a cup with cover have an average height (h) range of approximately 0.05~0.5 μm, and more suitably approximately 0.08~0.5 μm, and even more suitably approximately 0.1~0.25 μm, from the top face to its basal plane (if the top surface of the cover is flat, then the height is from the top flat surface to the basal plane, and if the top surface of the cover has a curvature that swells outward, then the height is from the top most part (a summit part) of the curvature to the basal plane), or contains ones having a height (h) range of approximately 0.05~0.5 μm, and more suitably approximately 0.08~0.5 μm, and even more suitably approximately 0.1~0.25 μm, from the top face to its basal plane (if the top surface of the cover is flat, then the height is from the top flat surface to the basal plane, and if the top surface of the cover has a curvature that swells outward, then the height is from the top most part of the curvature to the basal plane).

The surface diameter of the cover, of the cup-like structure that constitutes the structure of the aluminum hydroxide (an observation from the top), is approximately 50~750 nm, and more suitably approximately 120~380 nm, and even more suitably approximately 200~320 nm, and the surface diameter of the surface that adheres to the clay mineral has the same diameter or preferably a shorter diameter as the surface diameter of the cover part has, (or is much better if it is a little bit shorter), for example, it is approximately 50~410 nm, and more suitably approximately 80~330 nm, and even more suitably approximately 120~220 nm. Still, the measurements and numerical value ranges defined above are shown as the diameter of the longest part, if for example the shape of the cover part, when observed from above, or the part that adheres (basal plane) has a polygon shape, an elliptical shape, or any other shape that resembles these shapes and cannot be measured by a homogenous diameter length and is different by the position in which the diameter is measured.

[6] The composite pigment as defined above, wherein the structures in said form of a cup with cover, contain ones having a longitudinal direction cross-section (longitudinal cross section) shape, without the cover part, of a reverse trapezoid, or a quadrangle, or any shape that resembles these shapes.

Also, the corners formed by the merging of several planes may have a rounded edge, where a curved shape may be included in at least one part, and all these are included in the above-defined shapes.

[7] The composite pigment as defined above, wherein said aluminum hydroxide that adheres to the surface of said clay mineral is comprised of particles that have an average particle size of approximately 1~80 nm (0.001~0.08 μm), and more suitably approximately 10~50 nm (0.01~0.05 μm), and even more suitably approximately 20~40 nm, or includes particles that have a particle size of approximately 1~80 nm (0.001~0.08 μm), and more suitably approximately 10~50 nm (0.01~0.05 μm), and even more suitably approximately 20~40 nm.

In this way, the aluminum hydroxide: Al(OH)$_3$ particle that is used for the adhesion in this invention, may be in the Rayleigh region, in order to ensure a highly transparent particle (property).

Still, though the number of aluminum hydroxide particles, which constitutes the said cup-like structure with a cover, maybe be limited to just 1, it is normally constituted by multiple ultrafine particles defined above, which form this structure. In this invention, the cup-like structure, or the aforementioned muffin-like structure, may just be called "particle of cup-like structure", "particle of a muffin structure", etc.

[8] The composite pigment as defined above, wherein said clay mineral has a refractive index of approximately 1.40~1.80, and more suitably approximately 1.45~1.65, or includes a clay mineral with a refractive index of approximately 1.40 ~1.80, and more suitably approximately 1.45~1.65.

[9] The composite pigment as defined above, wherein said aluminum hydroxide adhered to said clay mineral exists at a range of approximately 3~75 weight %, and more suitably approximately 10~75 weight %, and even more suitably approximately 20~60 weight %, and even more suitably approximately 30~50 weight %, of the total weight of the clay mineral (the entire composite pigment) to which said aluminum hydroxide adheres, including said aluminum hydroxide.

[10] The composite pigment as defined above, further comprising a layer for covering the surface of said aluminum hydroxide.

[11] The composite pigment as defined above, wherein said layer has an average thickness range of approximately 0.001 ~0.5 μm, and more suitably approximately 0.01~0.4 μm, and even more suitably approximately 0. 03~0.2 μm, or includes one with a thickness range of approximately 0.001~0.5 μm, and more suitably approximately 0.01~0.4 μm, and even more suitably approximately 0.03~0.2 μm.

In this case, it is suitable to use an aluminum hydroxide particle that makes up the covered layer, which has a particle size or an average particle size of approximately 0.001~0.08 μm, and more suitably approximately 0.01~0.05 μm, and even more suitably approximately 0.03~0.05 μm.

[12] The composite pigment as defined above in [1] or [10], further comprising a silicone surface treatment layer.

[13] The composite pigment as defined above, wherein said aluminum hydroxide (particle) in the said form of a cup with cover exists at at least 30 weight % or so, and more suitably at least approximately 50 weight % or so, and even more suitably at least approximately 70 weight % or so, of the total aluminum hydroxide (particle) that adheres to the surface of said clay mineral.

Regarding the estimation of the shape of the cup-like structure with a cover, the vertical cross-sectional shape of the cup-like structure with a cover, can have any shape that resembles this structure, for example a reverse trapezoid shape obviously, or any quadrangle shape, where any of the edges may have a smoothed curve, and the cover may have a muffin-like curvature that swells outward, and any somewhat reverse trapezoid, and somewhat quadrangle shape, are all included when the mention of a structure of the particle, is described as a cup-like structure.

[14] The composite pigment as defined in claim 1, which comprises a clay mineral (powder particles, etc.) and an aluminum hydroxide (powder particles, or particle structure, particle edifice, etc.) that adheres to the surface thereof, and wherein 30% or more, or 30 weight % or more (more suitably 50% or more, or 50 weight % or more, and even more suitably 70% or more, or 70 weight % or more), of the entire adhered aluminum hydroxide particle, forms the aluminum hydroxide in the said form of a cup with a cover, adheres by its basal plane of the cup to the surface of said clay mineral, and has an average height, from the top surface of its cover part to its basal plane, of approximately 0.05~0.5 μm, more suitably approximately 0.08~0.5μm, and even more suitably approximately 0.1~0.25 μm.

The definition of the top surface of the cover part, and a scope for the cup-like structure with a cover, are as explained above.

[15] The composite pigment as defined in claim 1, wherein the basal plane of said aluminum hydroxide that adheres to the surface of said clay mineral (the contact area of the adhered aluminum hydroxide with the surface of the clay mineral), occupies approximately 3~95 weight %, and more suitably approximately 20~90%, and even more suitably approximately 50~90% of the total surface area of said clay mineral.

The total surface area of the said clay mineral represents the total surface area of the clay mineral, before the aluminum hydroxide is adhered, and it should be obvious that the sum of the surface area that does not have the adhered aluminum hydroxide, and the surface area that the aluminum hydroxide covers with its adhered basal plane (the contact area of the adhered aluminum hydroxide to the clay mineral) is what is defined as the total surface area.

[16] Cosmetics, comprising the composite pigment as defined in any one of claims 1~15 at a usage range of 1~100 weight %.

It is possible to optionally mix any other necessary components in order to fulfill the necessary types, forms, and purposes of cosmetics. Therefore, powders and composite pigments that were in use before may also be used. It is possible to suitably mix for example, this composite pigment at approximately 1~30 weight % in emulsification cosmetics, and approximately 1~80 weight % in solid powder cosmetics.

A SEM picture (×15,000) of Example 1 (covered composite pigment) is shown.

[FIG. 2]

A SEM picture (×50,000) of Example 1 (covered composite pigment) is shown.

Figure 3:
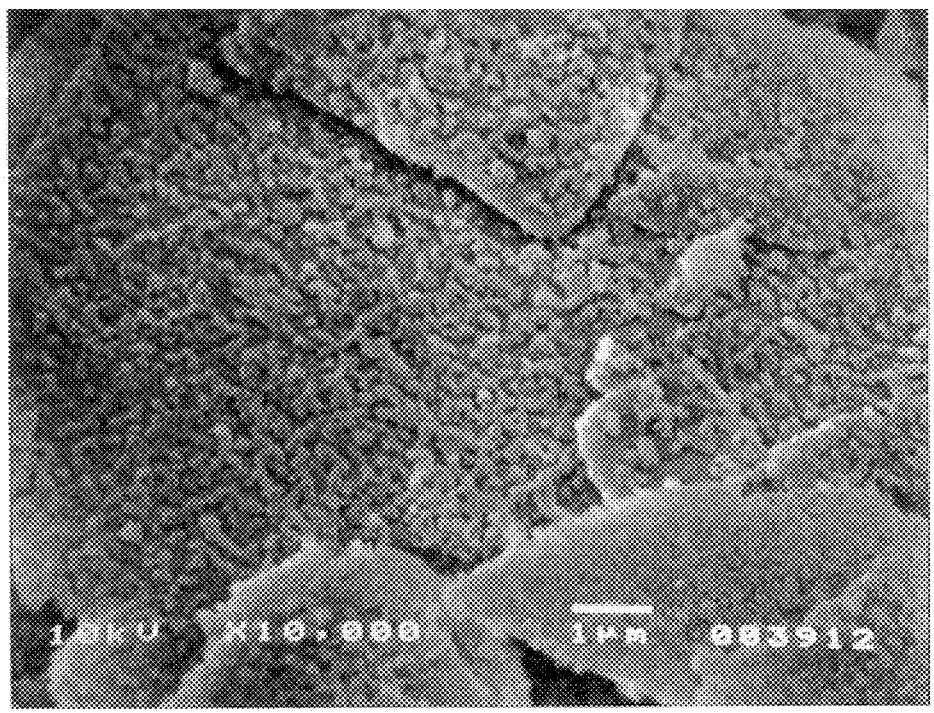

[FIG. 3] A SEM picture (×10,000) of Example 1 (covered composite pigment) is shown.

Figure 4:
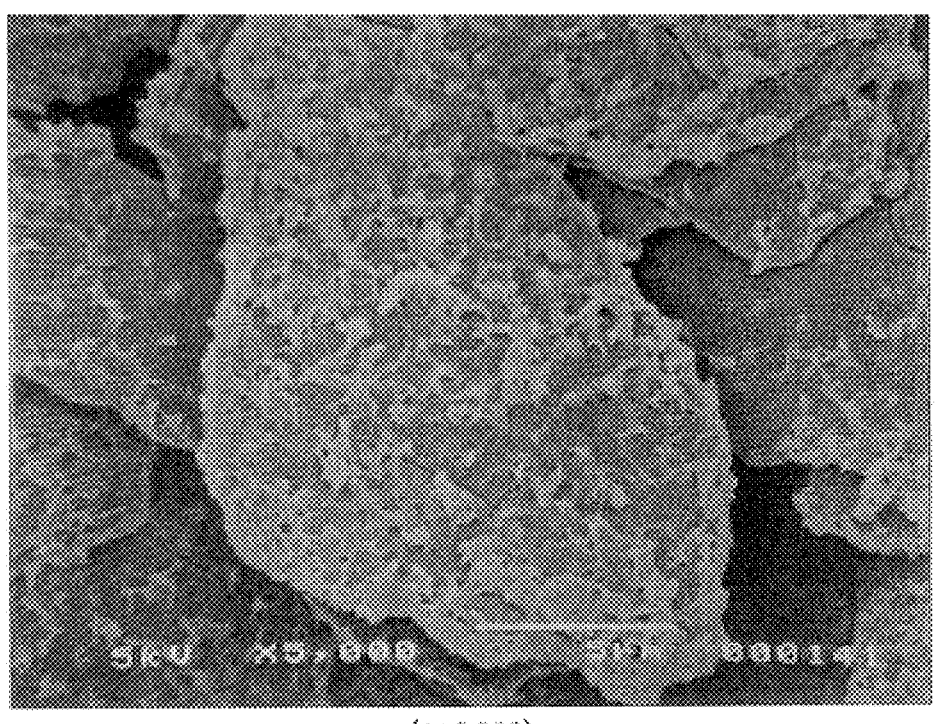

[FIG. 4] A SEM picture (×5,000) of Comparative Example 1 (covered powder) is shown.

Figure 5:
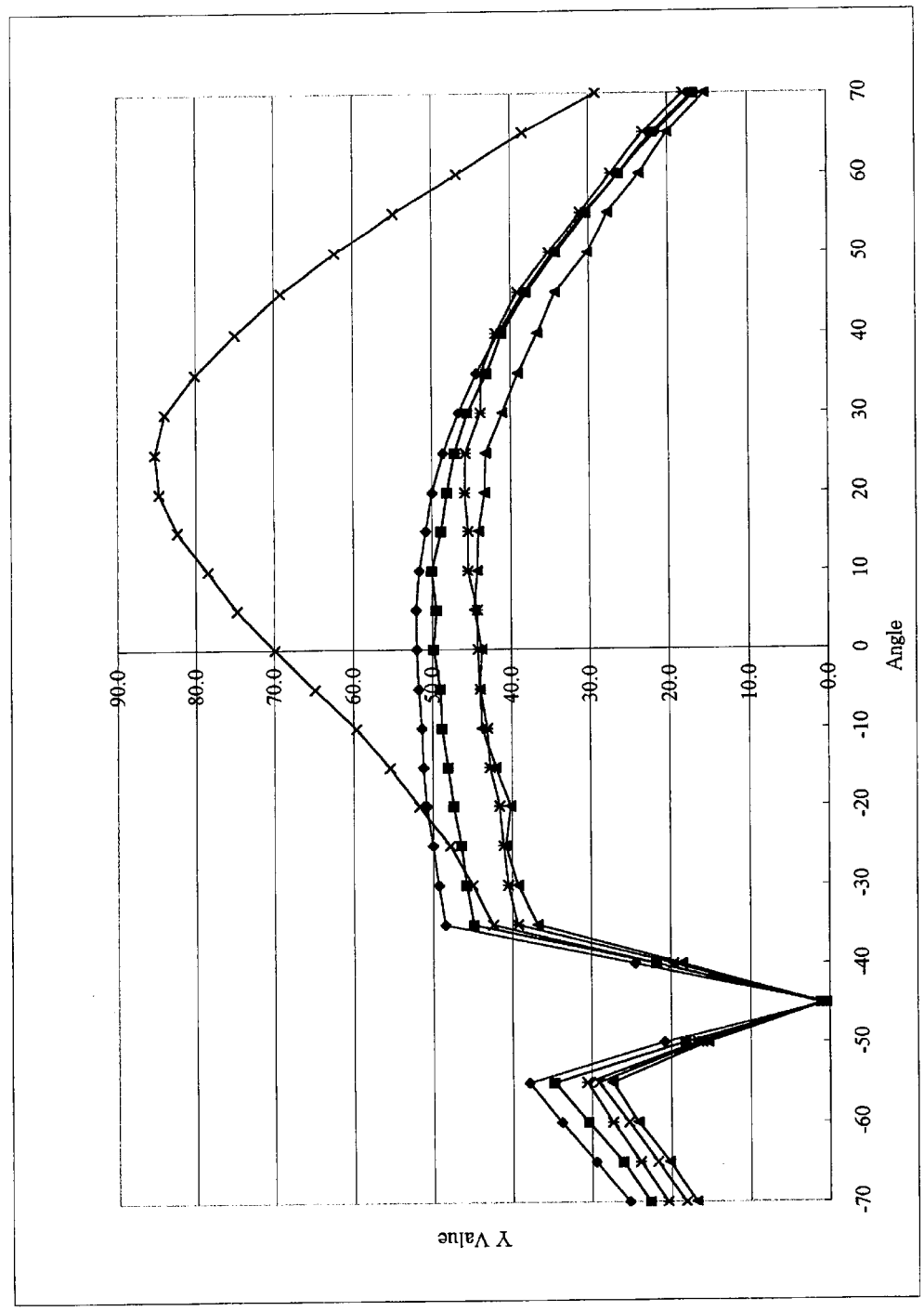

[FIG. 5] The Evaluation result made by the spectrophotogoniometer is shown.

Vertical Axis: Y value (Brightness) Horizontal Axis: Recipient angle (Degrees)

Within the graph: ◆: Example 1; ■:Example 2; *: Comparative Example 1; X: Mica; ▲: Skin is shown.

Figure 6A:
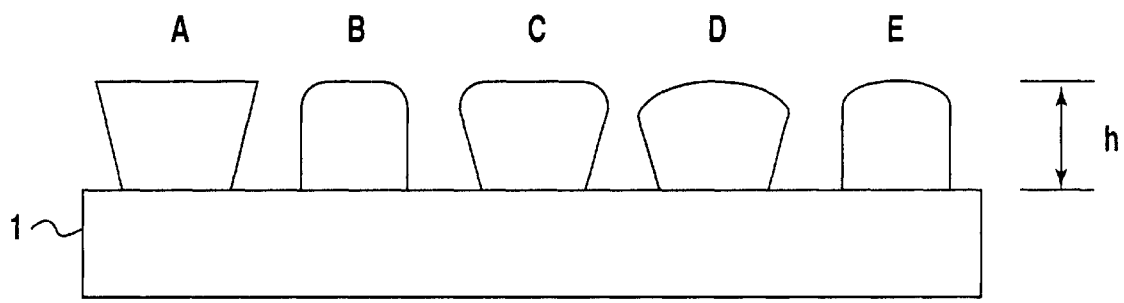
Figure 6B:
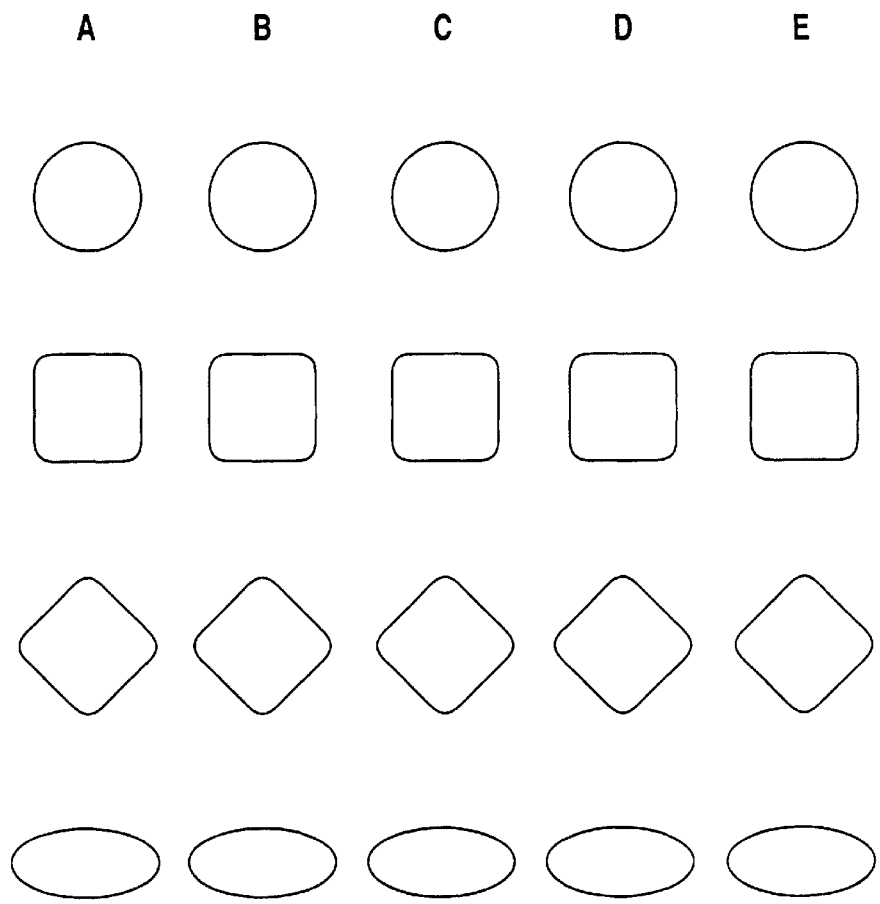

[FIG. 6]Representative structures, when viewing one of the surfaces of the clay mineral of the clay mineral-aluminum hydroxide composite particle, which comprises of the composite powder of the present invention, and aluminum hydroxide particles of specific structure that is adhered to said surface is lined up in a row, and a cross section in the longitudinal direction, is shown in FIG. 6(A). Within the particles that are lined up, a representative cross sectional shape in the lateral direction of FIG. 6(A) is shown in FIG 6(B).

[Description of the Code]

1: Clay mineral, A~E: a representative model of the specific structured aluminum hydroxide, h: height (the length from the cup basal plane to the top plane) of the cover).

DETAILED DESCRIPTION OF PREFERRED EMBODIMENTS

The actual implementation of the present invention is described here below, in a matter of explaining mainly the most suitable method (embodiments) for execution, where the actual scope of the present invention includes this suitable embodiments, however does not limit it to them.

The clay mineral that composes the composite pigment in the present invention can be of any type of mineral without any restrictions, if it belongs to the clay mineral group. For example, it is possible to name illite groups such as sericite (silky mica), muscovite, biotite, lithia mica, and synthetic mica, and kaolin groups such as kaolionite, nacrite, dekkite, halloysite, and, sillimanite groups such as sillimanite and kyanite, and magnesium silicate systems such as talc, and serpentine groups. The average particle size of said powders is suitably approximately 0.2~50 µm (laser diffraction method average particle size, made by HORIBA), and the average thickness of the said clay minerals is suitably approximately 0.1~1.5 µm (Measured by embedding the sample with resin and viewing it's cross sectional TEM picture). And, the clay mineral used in this invention has a refractive index suitably of approximately 1.40~1.80, and more suitably of approximately 1.45~1.65, and an average particle size of approximately 0.3~30 µm, and more suitably approximately 2 ~15 µm.

The composite pigment of this invention can have as its substrate particle, in place of the clay mineral, barium sulfate, or pearl pigments, for example silver or gold, or any iris foil pearl pigment, having an interference color of red, orange, green, blue, or, purple (including any iris foil pearl pigments covered with inorganic pigments, organic pigments, laked pigments, etc.), bismuth oxychloride, bismuth oxychloride coated mica, etc. With regard to the implementation of the above pigments, the characteristics of the barium sulfate and pearl pigment particles have the same average thickness, average particle size, and other said properties in the explanation of the clay minerals.

With regard to the structure of the clay mineral particles, it is more desirable to have a tabular form with a flat surface. Spherical structured clay minerals are also suitable. Within the clay minerals, mica, or other common illite group minerals such as sericite, muscovite, and synthetic mica, where the particles have tensile strength, is the most suitable, because the change of the particle size after pulverization is minimal with these particles.

Although the aluminum hydroxide particle that has a specific structure form of a cup with cover and adheres on the surface of the clay mineral may be of a crystal form, or a non-crystal form, the crystal form, which creates more lattice internal reflection, is more desirable. This refractive index is 1.56.

The amount of adhered aluminum hydroxide to be used, although different based on the type, average particle size, etc., of the clay mineral used in this invention, is approximately 10~75 weight %, and more suitably approximately 20~60 weight %, and even more suitably approximately 30~50 weight % of the aluminum hydroxide adhered clay mineral, in other words the entire composite pigment. When the amount is too abundant, the diffuse reflection of light increases and the transparent, brighter look becomes whiter, whereas when the amount is too scarce, the effect obtained in this present invention cannot be reached. With regards to the composite pigment, later described, that includes an ultrafine aluminum hydroxide particle covered layer (covered composite pigment), the total amount of aluminum hydroxide, including the aluminum hydroxide contained in the covered layer (the layer for covering the surface of the aluminum hydroxide), should be adjusted within the value range defined above in the compounding ratio thereof.

The aluminum hydroxide that contains a specific structure, which is used on the surface of the clay mineral for this invention, should be of a particle or particulate form. Although the surface of the clay mineral that has an aluminum hydroxide of this particle, or particulate form (multiple particles, or particulates) is prepared, and the powder containing a composite particle, which has an aluminum hydroxide adhered with a specific form, or a composite pigment which is composed of this particle (may be called a "composite pigment"), is what this invention calls a composite pigment, the structure and adhered form of the aluminum hydroxide particle, corresponding to its production conditions (also shown in the example section defined below), and the differences of the minute details of the surface of the clay mineral and differences of the surface activity of the aluminum hydroxide, maybe adjusted to conform to the specific structure and form of this invention.

The specific structure and form of the adhered particle, and the structure and form by which the particle adheres to the clay mineral, will impart a specific structure and the aluminum hydroxide particle which adheres to the particle surface of the clay mineral will impart a specific structure and at the same time will constitute a composite particle, which has the adhered aluminum hydroxide, and a powder which contains the said particle, is suitable as a powder for cosmetics. The composite pigment defined in this invention contains a particle, which includes the above said composite particle. The adhered aluminum hydroxide particle, which has the said specific structure, is more suitable if it is in the form of a cup-like structure with a cover, where the cup basal plane is adhered to the surface of the clay mineral, and is more suitable if the amount of specific structure and form, thus adhered on the clay mineral surface is more numerous.

The cup-like structure with a cover (i.e., the form of a cup with cover) does not have any restriction to its specific structure, but can be of any structure. It is possible that the surface of the cover part and side part take various structures in the range of which is usable for the purpose of a container as a cup.

By viewing from a horizontal plane, the perpendicular cross sectional shape with respect to the horizontal plane (the plane that is made when a cut through a perpendicular direction with respect to the cup basal plane of the cup-like structure is called the "longitudinal cross section", or "longitudinal direction cross section"), may be of a reverse trapezoid, or quadrangle shape, but can also be of a structure that is a muffin-like structure where the top surface of the cover part has a curved shape which swells outward (called "muffin-like") or any of these shapes which has a rounded edge (an edge that is produced from the merging of several planes). It may also be of any shape, which resembles the above shapes. As defined previously, the structure may be of any structure that is considered cup-like. The top surface of the cover part also does not have any restrictions, as long as the cover of the cup exists as a general top surface structure of a cover.

Similarly, the horizontal cross sectional shape (the plane that is made when a cut through a parallel direction with respect to the cup basal plane of the cup-like structure is called the "lateral cross section", or "lateral direction cross section") is the shape of the lateral cross section of the side part of the cup-like structure, and is represented by a circle, an ellipse, or a polygon (any tetrahedron, including a square or rectangle). A part of the edge of the polygon or all of the edges of the polygon may have a rounded edge where the surface is curved, and any shape that is similar to this shape or any shape that is similar to a part of this shape is included.

Above-defined cross sectional structure corresponds to the cup-like structure with a cover (the form of a cup with cover) that is an aluminum hydroxide that has a specific structure and adheres to the surface of the clay mineral defined in this invention.

In addition, it is desirable that the height (h) (called "height"), which is the length (the perpendicular length with respect to the basal plane) from the basal plane to the top face of the cover part of the cup-like structure (if the top surface of the cover part is flat, then to the flat surface, and if the surface is of a muffin-like structure, then to the swelled (in the upward direction) top-most part) be adjusted within a specific range.

The adherence of the aluminum hydroxide to the surface of the clay mineral as defined above, does not limit it to a single surface of the clay mineral, but is observed as uniform to all surfaces of the clay mineral, because it adheres (with the cup placed in the upright direction) to all surfaces as explained. The explanation of this invention is done with an intent as to having the surface, which has the cup adhered, facing up, where when viewed from a horizontal direction has the above defined cup-like structure placed on top of this surface. Therefore, when the opposite side of the clay mineral is observed, the cup-like structure is reversed and has its basal plane adhered to the surface of the clay mineral, and if one wishes to observed this opposite side as defined above, one needs to change the position of the cup so that it is facing upwards, when viewed from a horizontal plane, and then describe the structure of the adhered.

For the aluminum hydroxide that is adhered to the clay mineral powder, which is composed of the composite powder of this invention, it is desirable that the aluminum hydroxide of a specific adhered structure as defined in this invention, contains at least approximately 30 weight %, and more suitably at least approximately 50 weight %, and even more suitably at least approximately 70 weight % of the entire aluminum hydroxide adhered to the clay mineral. The total basal surface area (the contact surface of the adhered aluminum hydroxide and clay mineral) of the adhered aluminum hydroxide that has a specific structure, occupies approximately 3~95%, and more suitably approximately 10~95%, even more suitably approximately 20~90%, and even more suitably approximately 50~90%, of the total surface area (including the surface area occupied by the basal plane of the adhered aluminum hydroxide) of the clay mineral particle.

In FIG. 6, the longitudinal cross section shape (I), and lateral cross section shape (II), of a typical structure of an aluminum hydroxide, which has a specific structure, which is adhered to said surfaces of a clay mineral particle, is given as an example. FIG. 6-I shows perpendicular cut (longitudinal cross section) shapes of typical geometric models of A~E that is placed side-by-side on the horizontal plane on a single surface of the clay mineral. FIG. 6-II shows a representative example of a cross sectional shape of the cup side wall (i.e., cup side part surface), of the above defined model A~E. From one longitudinal cross sectional figure, several cross sectional shapes can be considered, and so some of the representative ones, are shown.

Models A, C, and D are considered reverse trapezoid (shape), while model B and E are quadrangle, and model D and E are considered muffin-like structures. In this invention, the surface by which the specific structure, which contains an aluminum hydroxide particle, is adhered to the surface of the clay mineral is called its "basal plane", and this is the basal plane of the said cup-like structure with cover. (i.e., the form of a cup with cover). Said basal plane and the top surface of the cover of the cup-like structure with a cover are parallel or somewhat parallel. The parallel direction described above is called the "lateral direction", and the perpendicular direction is called the "longitudinal direction". The reverse trapezoid (shape) described in this invention, means that the longitudinal cross section (cross sectional view in the horizontal direction) of the specific structure of the above described adhered cup-like structure, is of a reverse trapezoid shape (See model A, C, and D). Similarly, the cross section in the lateral direction "lateral cross section", describes the lateral direction cross sectional view of the cup (structure of the particle). The "height (h)" is, the height from the basal plane to the top surface of the cover part, and for a muffin-like structure, the distance from the basal plane to the upper most part of the swelled part, is the perpendicular length.

The structure of the outer surface of the cover part may be flat, or may have a gentle curved surface (muffin-like), which swells outward.

When the outer surface of the cover part is viewed from above, the shape is somewhat of a circle, an ellipse, a quadrangle, or any other polygon. In case of a polygon, it is desirable that the edges have roundness. As defined above, the structure of the surface of the cover part should be adequate to cover the top part of the cup (so as to not spill the contents of the cup).

The horizontal direction cross section (lateral cross section) of the cup side surface, has a shape that is a somewhat round shape, somewhat elliptical shape, or a polygon which has its corners jut outside. In this case, it is more desirable to have the edges of the polygon rounded. Regardless of the position (the perpendicular length from the basal plane) of the cross section, if this lateral cross section should have a uniform structure (the side plane has a cylindrical or prism shape), or as one gets closer towards the basal plane, the lateral cross sectional surface area gets wider (the shape produced by cutting along a horizontal direction of the uppermost part (head) of a cone shape or pyramid shape), or as one gets closer to the top part, the lateral cross sectional surface area gets wider (the shape produced by cutting along a horizontal direction of the uppermost part (head) of a cone shape or pyramid shape becomes the contact area, said reverse trapezoid shape), or the lateral cross sectional surface area of the middle part (half of the height from the basal plane to the upper plane), the shape (a reverse trapezoid shape, as defined above, or a shape that is similar to this) by which the lateral cross sectional surface area of the upper part (the position closest to the upper plane) gets wider, is the most suitable. When the cross section (longitudinal cross section) in the longitudinal direction (perpendicular direction) with respect to the cup basal plane is viewed, a quadrangle, rectangle, trapezoid, reverse trapezoid, or any other shape that is similar to these shapes is possible but, a shape that is a reverse trapezoid, or any shape that is similar to this, is most suitable. As defined above, the edges that are produced by the joining of two planes is more suitable if it is rounded.

The diameter of the surface of the cover part (when viewed from above), is correspondent to the diameter of the upper tip of the cup side part, and is approximately 50~750 nm in length, and more suitably approximately 120~380 nm, and even more suitably approximately 200~320 nm, and the diameter of the adhered plane (correspondent to the diameter of the lower tip of the cup side part) is preferably equal to the above defined diameter of the surface of the cover part, or shorter thereto, and approximately 50~410 nm, suitably approximately 80~330 nm, and more suitably approximately 120~220 nm. Still, with regard to the above-defined value of the diameter and range of values, if the shape of the cup part and adhered plane (basal plane), when viewed from above, is of a polygon shape or elliptical shape, the diameter of the longest part is shown.

It is more desirable to have the height of the specific structure: h (the height, namely the length from the cup basal plane to the top surface (i.e., top face, or topmost face, if any), is meant), to be adjusted so that they are nearly equal to each other when placed side-by-side, where the suitable height is approximately 0.05~0.5 $\mu$m, and more suitably approximately 0.08~0.5 $\mu$m, and even more suitably approximately 0.1~0.25 $\mu$m. It is more desirable to have the average height fall into these ranges.

In this way, it is more desirable to have the specific structure (the form of a cup with cover) composed of the aluminum hydroxide particle, be adhered onto the entire surface of the clay mineral in a uniform matter and as much as possible.

When the clay mineral surface of the composite powder is viewed from a diagonal angle from the top, several shapes such as a cube, parallelepiped rectangle, cylinder, angular tube, truncated cone, converse truncated cone (a truncated cone that is made upside down), truncated pyramid, reverse truncated pyramid (a truncated pyramid that is made upside down), and said shapes that have at least one of its edges created by the conjunction of several planes rounded off, may be present.

In this way a composite pigment, containing the specific structures containing aluminum hydroxide particles that is adhered onto a clay mineral, which has its surface further covered with a layer of aluminum hydroxide, will further augment the effects of the purpose of this invention. The average thickness is suitably approximately 0. 001~0.5 $\mu$m, and more suitably approximately 0.01~0.4 $\mu$m, and even more suitably approximately 0.03~0.2 $\mu$m. And the particle size of the aluminum hydroxide particle that composes the covered layer is suitable if it is an ultrafine particle, where the average particle size is approximately 0.001~0.08 $\mu$m, and more suitably approximately 0.01~0.05 $\mu$m, and even more suitably approximately 0.03~0.05 $\mu$m. Still, the condition of the covered layer (structure of the covered layer) is completely different from just covering with granular, spherical, needle-shape, spindle-shape, or honeycomb shaped particles.

When the average particle size of the clay mineral is under 0.2 $\mu$m, the phase scattering increases, and the transparency is lost, increasing the opacity, and thereby creating a material that is not fit for the purpose of this invention. And, when the average particle size is over 50 $\mu$m, a rough feeling and discomfort on the skin emerges, which comes from the size of the powder particle, and thus is not desirable.

When the surface of the composite pigment, which consists of a clay mineral and an aluminum hydroxide that has a specific structure, is coated with another layer of aluminum hydroxide, and when the average thickness of the clay mineral (thickness defined here means the length of the shortest distance between one plane of the particle and its opposite side), is less than 0.05 $\mu$m, the tensile strength of the clay mineral increases, but the amount of transmitted light is too large so that the amount of light that is reflected back from the surface and internal part of the clay mineral is too small, and thus undesirable. And, when the average thickness is greater than 1.5 $\mu$m, there is no difference in the internal scattering of light that occurs in the internal part of the covered layer. In addition, it is not desirable when the average thickness is greater than 1.5 $\mu$m, because the tensile strength of some types of clay minerals decreases, and the transparency of the covered pigment decreases as well.

The refractive index of the aluminum hydroxide that is adhered to the clay mineral, which is a substrate of the powder, which is obtained by selecting an aluminum hydroxide particle, has a specific structure, and is adhered to the surface of a clay mineral, is 1.56. In this case, the environment surrounding the specific structured aluminum hydroxide particle, and the interaction between the diffuse reflection and transmittance of light, along with its refractive index, that comes from the structure itself of the said aluminum hydroxide, balances the scattering and transmittance of light, which produces a makeup film that has a bright, natural finish, without any color drabness, due to the adjusted scattering effect of light.

When the said ultrafine particle of aluminum hydroxide is covered on top of a clay mineral, which has its surface adhered with specific structures of aluminum hydroxide, which is the covered composite pigment, and the thickness of the covered layer is beyond 0.5 $\mu$m, the effect of the internal scattering effect of light on the environment surrounding the aluminum hydroxide ultrafine particle within the covered layer, is too strong, and the transparency becomes low, creating a whitish color, thereby making it hard to create a highly transparent product that makes the skin color look brighter. On the other hand, when the thickness is lower than 0.001 $\mu$m, the internal scattering of light cannot be expected. By utilizing the irregular reflection effect of light created by the specific structure and adhered structure (especially, when the longitudinal cross section, which is perpendicular with respect to the adhered basal plane, of the specific structure is of a reverse trapezoid shape, [when the structure is of a muffin-like structure, the surface of the cover is curved] or any structure which is similar to this, for example, a crystal form) of the aluminum hydroxide of this invention, it is possible to produce a transparent and brighter finish of the skin color. In this case, the height: h from the adhered plane to the topmost part of the cover, in other words the cover surface, and in the case of a muffin-like structure, the topmost part, of the structure and adhered structure (especially said reverse trapezoid and any crystal form which resembles this shape) of the aluminum hydroxide specified above, should be made longer in order to increase the amount of light that directly hits the clay mineral surface. In this case, in order to produce a transparent and highly brighter skin color, it is suitable to make the said height (h) approximately 0.05~0.5 $\mu$m, and more suitably approximately 0.08~0.5 $\mu$m, and even more suitably approximately 0.1~0.25 $\mu$m.

When the above defined height is below 0.051 μm, the light then hits the clay mineral directly, producing very little scattered light and increased transmitted light, and therefore, the objective of getting a high transparency, and an effect of making the skin look brighter cannot be reached, and actually produces a luster of the clay mineral itself, making the troubled morphology of the skin stand out. And, when said height is above 0.05 μm, the scattering light effect will make the troubled morphology of the skin and troubled skin tone less noticeable (makes wrinkles, blemishes, etc. less noticeable), but will also make anon-transparent and white finishing effect, because the scattering light effect is too strong.

As defined above, the aluminum hydroxide adhered composite pigment of the present invention may have covered (an aluminum hydroxide layer) on its surface, another layer of aluminum hydroxide (preferably its ultrafine particle), or a surface treated layer of silicone surface treatment. By utilizing these types of covered layers or surface treatment layers, the objective of this invention is increased to a higher extent.

(Method of Production)

There are no difficult points to the production of the composite pigment of the present invention. The composite pigment can be easily produced based on the descriptions, as explained by the specification of the present application, particularly the examples shown later with more detail, however there are some additional details that need to be added, as described below.

Purified water is used at approximately 3~15 times (weight) the amount of clay mineral used (if barium sulfate, or pearl pigments are used instead of clay minerals, then 3~15 times the amount of barium sulfate or pearl pigments). In order to prepare the aluminum hydroxide, the amount of aluminum salt used is approximately 2~75 weight % of the gross weight of material including the clay mineral. Dissolve the aluminum salt in purified water, and homogeneously disperse the clay mineral in the solution, and heat to approximately 5~100° C., and add a seed crystal and mix. Then decrease the temperature of the solution to approximately 40~−10° C. Filtering the aqueous solution, and drying the product produces a composite pigment containing clay minerals with adhered aluminum hydroxide.

In order to produce a covered composite pigment, which has as an additional covered layer consisting of aluminum hydroxide ultrafine particles, use the aqueous solution of the above defined composite pigment that is decreased to a temperature of 40~−10° C., and neutralize the solution to a pH range of 7~10 by using inorganic acids or acidic gas, then filter the solution and wash with water, and then dry the product at 40~130° C.

In order to impart a silicone surface treatment, a commonly used method (for example, see Japanese Patent Kokai Publication JP-A-9-48716) may be used on the aluminum hydroxide adhered clay mineral (Composite Pigment), or said composite pigment with an additional covered layer of ultrafine particles of aluminum hydroxide (Covered Composite Pigment).

It is possible to include the composite pigments (which also includes covered composite pigments, and silicone surface treated composite pigment as described above) of the present invention in cosmetics, and in this case, there are no limits to the amount of composite pigment to be used (quantity). For example, it is possible to suitably mix approximately 1~100 weight % (weight % is weight standard for all composition) in case of cosmetics of a powder form. In case of cosmetics of cake forms or paste forms, it is possible to suitably mix approximately 1~100 weight %, and more suitably approximately 1~180 weight %, of the total weight of all the powder ingredients. And, in case of cosmetics of emulsified products such as milky lotions, it is possible to suitably mix approximately 1~60 weight %, and more suitably approximately 1~30 weight %, of the total weight of all the emulsified product ingredients. The composite pigment of this invention is especially most suitable for makeups, such as, foundations, face powders, eye shadows, blushes, creams, milky lotions, skin lotions, nail colors, lipsticks, etc. In order to put in cosmetics, the composite pigment of this invention may have a surface treatment, as the above defined silicone treatment, as well as other surface treatments such as fluorine treatment, lecithin treatment, amino acid treatment, metal soap treatment, surfactant treatment, and other combinations of treatments that may include the silicone treatment, if necessary.

Next, one of the common methods of making wrinkles less noticeable is to attach polymer resins to the surface of substrates (clay minerals), and produce ruggedness, created by the polymers, and produce a diffused reflection of light. Another method is to structure the powder into a butterfly shape, so as to produce diffuse scattering of light, by the complicated structure. Both of these methods use the effect of diffuse reflection of light on the surface of the material. The present invention, by using an aluminum hydroxide particle, with a specific refractive index (1.56), that has a specific particle structure and structure (the basal plane of the cup, of the cup-like structure with a cover, adhered: especially, with the said reverse trapezoid structure (form), or any other structure that resembles this) as defined above, attached to the surface of a substrate, and especially suitable is that the adhered particle of the specific structure is adjusted to the above defined height: h, to a specific range, where the interaction between the refractive index of the adhered particle, and clay mineral adjusts the balance between the amount of transmitted light and reflected light, lessens the amount of light that directly hits the clay mineral, and adjusts the effect of diffuse reflective light. As a result, the troubled morphology of the skin and skin tone can be hidden (wrinkles and blemishes are harder to see), while still maintaining a transparent look, which makes a drabbed skin color look brighter and more beautiful.

And by placing an ultrafine aluminum hydroxide particle layer, which is adjusted so that the thickness covered on the surface of the above defined composite pigment is within a specific range, the environment surrounding the particle within the ultrafine particle layer, creates an effect of internal scattering of light, and has a refractive index (1.56) that is close to the stratum corneum of the skin, and by utilizing the effect of scattering light that is produced from the above defined specific structure of the adhered particle, the troubled morphology of the skin and color tone of the skin, such as wrinkles and blemishes become burred and less noticeable (the hiding effect of the troubled morphology of the skin and troubled color tone of skin), while still maintaining transparency, and makes the skin color look brighter. The invention of this composite pigment, by comparing the invention as defined in the Japanese Patent Kokai Publication JP-9-20609, the hiding effect of the troubled morphology of the skin, and hiding effect of the color tone of the skin is superior, while being able to change the color drabness of the skin to a transparent and brighter finish.

The composite pigment of this invention, when compared to the invention defined in TOKKAIHEI 9-20609, is clearly much smoother. The invention defined in the Japanese Patent Kokai Publication JP-9-20609, has the outer most layer (part) of the composite pigment, of a honeycomb structure, where the surface is remarkably rugged. For this reason, when applied to the skin, the spreadability on the skin is bad, and a burden on the skin occurs, because of the interaction between this and the ruggedness of the skin. And because the ultrafine particles that make up the outer most layer is non-uniform, as well as having a large surface area, its ability to absorb water and oil on the skin becomes high, thereby making the spreadability bad, and the feeling on the skin very heavy.

Compared to this, the composite pigment of the present invention, which contains a clay mineral, and an aluminum hydroxide that has an aluminum hydroxide particle of a specific structure, which is adhered to the surface of the clay mineral. The aluminum hydroxide particles comprises of a structure that is of a cup-like structure with a cover, where the basal plane is adhered to the surface of the clay mineral, and are more suitable if there are many adhered to the surface of the clay mineral, where the height (h) is adjusted so that they are uniform, and the longitudinal cross section is of a reverse trapezoid shape or any shape that is similar. And as can be understood from an observation of a high magnification TEM picture (see FIGS. 1–3), the above defined reverse trapezoid shape is of a layer form, where it is laminated as if it is covered, so that a smooth feeling seems to be obtained.

And, it seems that the composite pigment of this invention, as defined above, which preferably is covered with aluminum hydroxide (suitably ultrafine particles) gets its good feeling, because of the smooth surface that is in contact with the skin, and because the contact surface area of the covered aluminum hydroxide with the skin is comparatively low, due to the structure of the said aluminum hydroxide.

Cosmetics of the present invention can have other ingredients, besides the composite pigment of the present invention (including said covered composite pigment, or silicone treated composite pigment), that are normally used in cosmetics, when needed. For example, inorganic powders such as talc, kaolin, sericite, muscovite, phlogopite, red mica, biotite, synthetic mica, lithia mica, vermiculite, magnesium carbonate, calcium carbonate, diatomite, magnesium silicate, calcium silicate, aluminum silicate, barium silicate, barium sulfate, strontium silicate, wolframic acid metal salt, or silica, hydroxyapatite, zeolite, boron nitride, ceramic powder, organic powders such as nylon powder, polyethylene powder, polystyrene powder, benzoguanamine powder, polyfluoridation ethylene powder, di-styrene benzene polymer powder, epoxy powder, acrylic powder, silicone powder, microcrystalline cellulose, inorganic white pigments such as titanium dioxide and zinc oxide, inorganic red system pigments such as iron oxide (red iron oxide) and titanic acid irons, inorganic brown system pigments such as γ iron oxides, inorganic yellow system pigments such as yellow soil and yellow iron oxides, inorganic black color system pigments such as tetravalent acid iron oxide, carbon black, inorganic violet system pigments such as mango violet, cobalt violet, inorganic green system pigments such as chromium oxide, chromium hydroxide, and titanic acid cobalt, inorganic blue system pigments such as ultramarine blue, and prussian blue, pearl pigments such as titanium dioxide covered mica, titanium dioxide covered bismuth oxychloride, bismuth oxychloride, titanium dioxide covered talc, fish scale foil, colored titanium dioxide covered mica, metal powder pigment such as aluminum powder, copper powder, colored composite pigments such as iron-doped zinc oxide and iron-doped titanium dioxide, Organic pigments such as red No.201, red No.202, red No.204, red No.205, red No.220, red No.226, red No.228, red No.405, orange-colored No.203, orange-colored No.204, yellow No.205, yellow No.401 and blue No.404, organic chlorophyll pigment such as FD&C Red No.3, red No.104, red No.106, red No.227, red No.230, red No.401, red No.505, orange-colored No.205, FD&C Yellow No.4, yellow No.5, yellow No.202, yellow No.203, orange-colored No.3 and zirconium, barium, or aluminum lake of blue No.1, natural colorants such as β-carotene, hydrocarbon oils such as squalane, mineral oil, vaseline, micro crystalline wax, ozokerite, ceresin, myristic acid, palmitic acid, stearic acid, oleic acid, iso-stearic acid, cetyl alcohol, hexadecyl alcohol, oleyl alcohol, cetyl 2-ethylhexanoate, 2-ethylhexyl palmitate, 2-octyldodecyl myristate, neo-pentylglycol di-2-ethylhexanoate, glyceryl tri-2-ethylhexanoate, 2-octyldocyl oleate, isopropyl myristate, glyceryl triisostearate, caprylic/capric triglyceride, olive oil, avocado oil, yellow bees wax, myristyl myristate, mink oil, lanolin oil, silicone oil, higher fatty acid oil, ester oils of fatty acids, higher alcohol, oil components of wax groups, and organic solvents such as acetone, toluene, butyl acetate, and ester acetate can be used in various amounts.

Resins such as alkyd resin, urea-formaldehyde resin, plasticizers such as camphor, acetyl tributyl citric acid, ultraviolet absorbing agents, antioxidants, antiseptics, surfactants, moisturizing agents, perfumes, water, alcohol, and thickeners can also be used.

There are no restrictions to the form of cosmetics in which the present invention can be used. For example the present invention can be used in several forms such as powder form, cake form, pencil and stick form, pellet form, ointment form, liquid form, milky lotion form, or cream form. The composite pigment of this invention, especially when using mica as the clay mineral for the composite pigment, although is very useful as cosmetics, can be very useful in various other fields besides cosmetics, such as for industrial purposes, such as inks, paints (coating), plastics, rubber additives, rubber moldings, rubber mold separating material etc., and other various lubricants.

This application is based on Japanese Patent Application Serial No. 2000-265026, filed on 1 Sep. 1, 2000, and Japanese Patent Application Serial No. 2000-034766, filed on Feb. 14, 2000, each of which is incorporated herein by reference in their entirety.

EXAMPLES

Although the examples and comparative examples for the present invention are shown below in detail, they do not restrict the present invention to such. The evaluation of gloss, wrinkles, blurring effect of blemishes, drabness of color, and smoothness, of the example and comparative example were preformed, by the method as shown below. Also, the composition ratios in the examples are all shown as parts by weight.

[Evaluation of the Gloss by a Spectrophotogoniometer]

The sample was applied near the base of palm of the hand, at an amount of 1.25 mg/cm$^2$, and an evaluation was made by using a spectrophotogoniometer (NIPPON DENSHOKU CO., LTD.) set at a light incident angle of 45°, and changing the light reception angle from −70~70°.

[Evaluation of Wrinkle]

A silicon replica of the groove of the area from the cheek to the nose was made, and the sample was applied on this surface with a blush at an amount of 0.4 mg/cm², after which a picture was taken. A panel of 25 persons evaluated the picture of the above replica, to assess the noticeable level of the wrinkles.

[The Gradation Effect of Blemish]

After homogeneously blending 3.5 g of the sample with 10 g of caster oil, a film, with a thickness of 28 $\mu$m, was made on a glass slide with a doctor blade. A colored paper that imitates skin with fair complexion was prepared, on which 0.5 mm diameter small identical circles of a light brown color was placed. The thin film of the sample that was prepared above, was placed over the skin colored paper, and the brown colored spots were visually evaluated against the background fair skin colored paper to asses the noticeable level of blemishes.

[Evaluation of the Color Drabness by Wetting with Oil]

The color of dry powder was measured by placing the sample in a quartz cell and evaluated by spectral analysis, while the color of the wet powder was measured by blending each sample with mineral oil at its oil absorption, and evaluating its color by spectral analysis. The degree of drabness was measured from the $\Delta$E value (color difference) between the color of dry powder and the color of wet powder (wet powder color), and the movement (direction and degree of movement) of the chroma.

[Evaluation of Smoothness by Measurement of Coefficient of Dynamic Friction]

The smoothness was measured by having the friction sensory tester (Kato Tech, Inc.) slide over the samples 5 times, where the value (MIU) of the $_5$th time was recorded.

Example 1

Disperse 252 g of muscovite into a solution, which is comprised of 168 g of sodium aluminate dissolved in 2,520 ml of purified water. After uniformly dispersing the solution, increase the temperature to 95° C. Add to this solution, 0.84 g of aluminum hydroxide, and cool to 80° C. with cold water, and then cool quickly to 20° C. again with ice-water. Afterwards, a maturing reaction was carried out in 8 hours, while maintaining the temperature below 20° C. Add hydrochloric acid to the reacted solution, to neutralize it at a pH of 8.0, and then filter and dry in order to obtain adhered particles (composite pigments), which have many specific structures of reverse trapezoid structured aluminum hydroxide (crystal) adhered to the surface of muscovite, to which on the surface, ultrafine particles of aluminum hydroxide (average particle size: 0.1 $\mu$m) are covered (thickness approximately 0.08 $\mu$m) to yield the covered composite pigments.

The above-mentioned reverse trapezoid shape is, as defined earlier, a shape produced by the perpendicular (longitudinal) cross section of the specific structure adhered to and with respect to the surface of the muscovite (horizontal direction), which is of a reverse trapezoid shape with respect to the muscovite basal plane.

The content of the aluminum hydroxide with respect to the entire covered composite particle is approximately 36 weight %.

Figure 1:
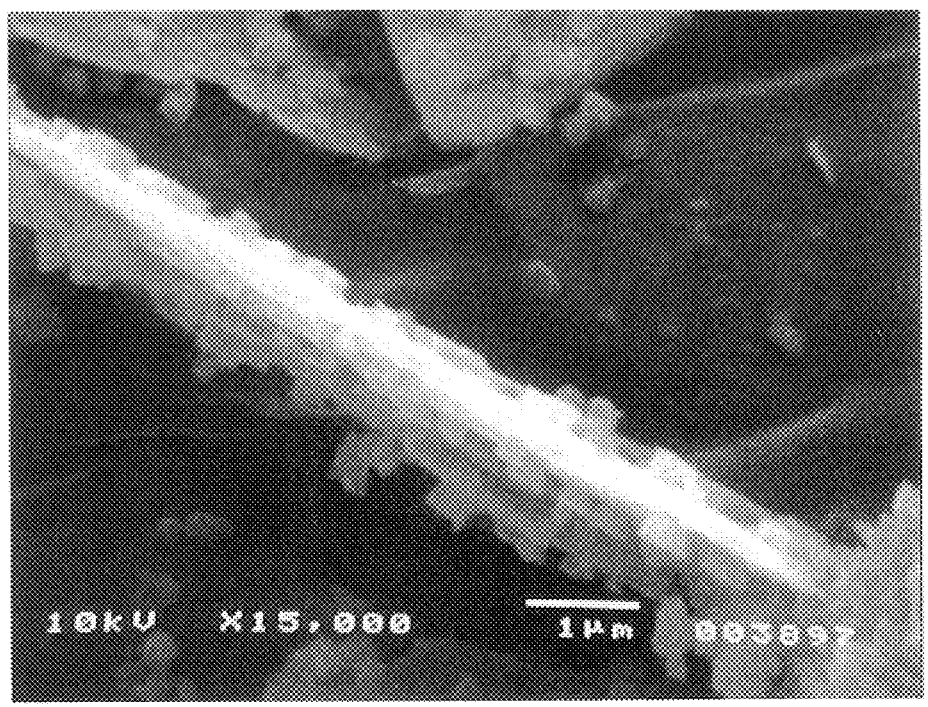
[FIG. 1]
Figure 2:
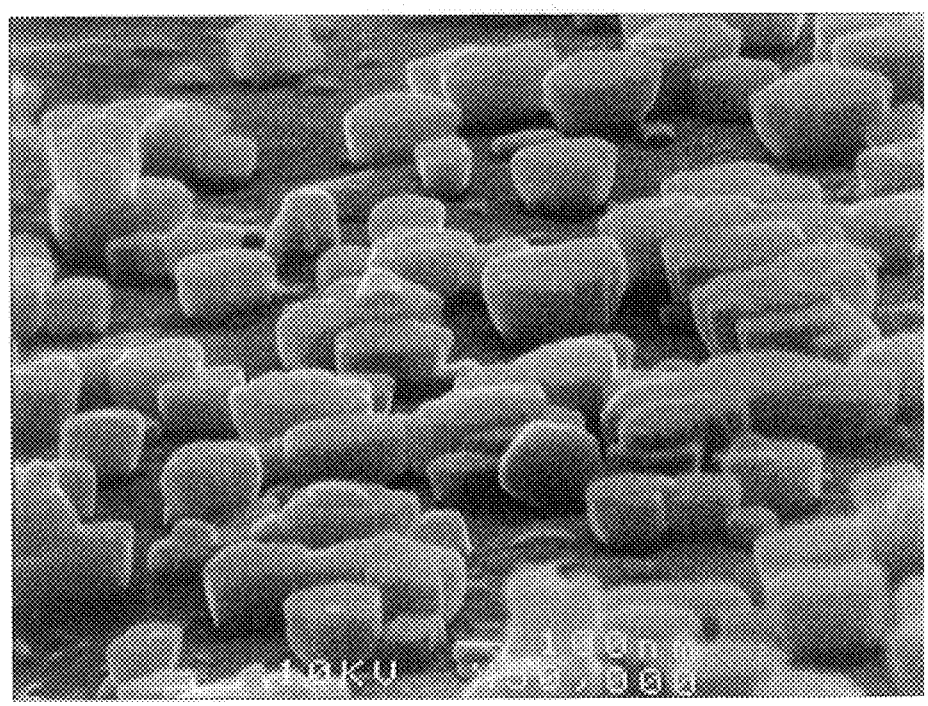

A SEM picture of the obtained covered composite pigment was taken, and is shown in FIG. 1 (×15,000), FIG. 2 (×50,000), and FIG. 3 (×10,000). It can be seen from these figures that the product of the present invention includes many adhered particles comprised of cup-like structure with cover (form of a cup with cover), where the longitudinal cross sectional shape is of a reverse trapezoid shape with respect to the muscovite basal plane, and the height (height of the adhered particle comprised of the specific structure: 0.1 $\mu$m) is maintained as nearly equal.

Example 2

A process similar to that of Example 1, aside from not neutralizing the solution after the maturing reaction of 8 hours, but filtering and drying the product directly, was repeated. A composite pigment, which has particles of aluminum hydroxide particles composed of a reverse trapezoid shape adhered to the surface of muscovite, was obtained.

Example 3

Heat 302 ml of ion-exchanged water to 90° C., after which 40.26 g of sodium aluminate is added, and is further heated to 95° C. After reaching 95° C., add 100 g of pearl pigments (made by Merck & Co., Inc.) and disperse until homogenous, and then add 30 g of the supernatant of a aluminum hydroxide solution (supernatant of a dispersed solution of 1.5% aluminum hydroxide), and agitate for 10 minutes. Afterwards, cool to 70° C. with cold water, and then cool rapidly to below 20° C. with ice-water and carry out a maturing reaction for 7 hours. After this reaction is over, filter, wash with water several times, and dry, to obtain an aluminum hydroxide of muffin-like structure (height of 0.1 $\mu$m, diameter of 0.2 $\mu$m) adhered composite pigment.

Example 4

Dissolve 32.76 g of aluminum chloride hexahydrate into 167 ml of purifiedwater. After dispersing 11.14 g of sericite into the obtained solution, increase the temperature until solution boils. Add 60 g of the supernatant of 1.5% aluminum hydroxide solution to the boiled solution. To this, an alkaline solution of 11.75 g of sodium hydroxide dissolved in 200 mL of purified water, which was prepared separately, was added drop wise and cooled to 70° C. with cold water. The solution was further cooled down to below 20° C. rapidly with ice-water, and was sustained for 12 hours. After filtering, washing with water several times, and drying, a composite pigment, which has aluminum hydroxides (height of 0.15 $\mu$m, diameter of 0.3 $\mu$m) composed of a cup-like structure (the form of a cup with cover adhered to the surface of sericite), was obtained.

Comparative Example 1

[JP-A-9-20609 Described in the Manufacturing Method]

After dissolving 400 g of aluminum sulfate to 2000 ml of purified water, add 200 g of muscovite and mix until homogenous. To this dispersed solution, add 457 g of urea and treat at 95° C. for 6 hours, and then cool, and after washing with water, wash with ethanol, and dry at 70° C. to obtain an aluminum hydroxide covered powder.

FIG. 4 (×5,000) shows the SEM picture result of the obtained covered powder. It can be seen from this figure, that the surface of the particle powder, which has a honeycomb structure, is remarkably corrugated.

Example 5

Production of a Powder Foundation

| Ingredient No. | Ingredient | Weight parts |
|---|---|---|
| (1) | Silicone treated Muscovite (Covered composite pigment; from Example 1) | 40 |
| (2) | Silicone treated Sericite | 20 |
| (3) | Silicone treated Talc | 15 |
| (4) | Silicone treated Titanium Dioxide | 3 |
| (5) | Polyethylene Beads | 10 |
| (6) | Red Iron Oxide | 3 |
| (7) | Silicone Oil | 9 |

[Method of Production]

Mix powder ingredients (1)~(5) from above in a henschel mixer and agitate at low speed for 4 minutes, and then take out the mixed product and pulverize. Return the pulverized powder to the henschel again, and add ingredients (6) and (7) and after agitating for 10 minutes, take out and pulverize (HOSOKAWA MICRON Inc.), sort with an approximately 400 μm-mesh screen, and add to a tray to obtain the desired product.

Example 6

Production of an Emulsified Foundation

| Ingredient No. | Ingredient | Weight parts |
|---|---|---|
| (1) | Stearic Acid | 1.75 |
| (2) | Octyldodecyl Myristate | 4.0 |
| (3) | Squalane | 11.0 |
| (4) | Polyethylene Glycol Monostearate | 2.0 |
| (5) | Glyceryl Monostearate | 3.0 |
| (6) | Cetyl Alcohol | 0.3 |
| (7) | Pigment | 4.0 |
| (8) | Butylparaben | 0.1 |
| (9) | Composite Pigment (Example 2) | 18.0 |
| (10) | Carboxymethylcellulose Salt | 0.1 |
| (11) | Methylparaben | 0.2 |
| (12) | Triethanolamine | 0.7 |
| (13) | Glycerine | 6.0 |
| (14) | Purified Water | 48.55 |
| (15) | Perfume | 0.3 |

[Method of Production]

Mix and heat ingredients (1)~(8) at 85° C. until ingredients are completely dissolved, and add ingredient (9) and disperse until uniform. Gradually add to this, a mixture of ingredients (10)~(14), which was heated at 85° C. and dissolved separately, and emulsify. After maintaining the emulsified temperature and agitating for 13 minutes, cool down to 50° C. while agitating. To this, add ingredient (15) and cool down to 40° C., and take out product and transfer to a container to obtain an emulsified foundation of this invention.

Example 7

Production of an Oil-Based Foundation

| Ingredient No. | Ingredient | Weight parts |
|---|---|---|
| (1) | Squalane | 66.8 |
| (2) | Octyldodecyl Oleate | 5.0 |
| (3) | Microcrystalline Wax | 5.5 |
| (4) | Polyethylene Wax | 0.5 |
| (5) | Colored Pigments | 12.0 |
| (6) | Covered Composite Pigment (Example 1) | 9.0 |
| (7) | Composite Pigment (Example 2) | 1.0 |
| (8) | Perfume | 0.2 |

[Method of Production]

After heating and dissolving the above ingredients (1)~(4) at 85° C., increase the temperature to 100° C. Then return the temperature to 85° C., and confirm that the ingredients are completely dissolved. Add to this, ingredients (5)~(7) and agitate until dispersed homogenously. Afterwards, a vacuum-defoaming process was carried out, and ingredient (8) was added, and transferred to a container to obtain an oil-based foundation of this invention.

Comparative Example 2

This comparative example was prepared similarly to Example 5, aside from using the covered powder (production method of Japanese Patent Kokai Publication JP-A-9-20609 was used) obtained from Comparative Example 1, instead of the silicone treated muscovite (covered composite pigment; Example 1).

Comparative Example 3

This comparative example was prepared similarly to example 5, aside from using the composite pigment (silicone treated) obtained from Comparative Example 2, instead of the silicone treated muscovite (covered composite pigment; Example 1).

Comparative Example 4

This comparative example was prepared by repeating Example 5, aside from using muscovite (silicone treated), instead of the silicone treated muscovite (covered composite pigment; Example 1).

[Feel : Evaluation of Smoothness]
[Measurement of Coefficient of Dynamic Friction (Measurement of Smoothness)]

A measurement of smoothness was performed by the method defined above, to obtain a coefficient of dynamic friction for each sample. The results were as follows. The silicone treatment of 4% is a treatment by α-triethoxy polydimethylpolysiloxane.

| Sample | Untreated ($\times 10^{-1}$) | Silicone Treated ($\times 10^{-1}$) |
|---|---|---|
| Example 1 | 2.20 | 1.94 |
| Example 2 | 2.16 | 1.90 |
| Comparative Example 1 | 3.35 | 3.05 |

-continued

| Sample | Untreated (× 10⁻¹) | Silicone Treated (× 10⁻¹) |
|---|---|---|
| Muscovite | 2.91 | 2.24 |
| Sericite | 2.23 | 1.97 |

Lower numbers represents better smoothness in the table above, and as the results show, the present invention is the same or is better in smoothness when compared with sericite, which is considered to have good smoothness as a pigment usable for cosmetics. In addition, it can be seen that the effect is remarkably improved with the use of a silicone treatment.

[Evaluation of Color Drabness]

The drabness of color was evaluated for each sample, according to the above-defined method. The results were as follows. The 'L', 'a', and 'b' value shown below represent the Hunter equation values where 'L' represents brightness, 'a' represents the degree of redness, and 'b' represents the degree of yellowness.

|  | Dry Powder | | | Wet Powder | | | Δ E (Color |
|---|---|---|---|---|---|---|---|
| Sample | L | a | b | L | a | B | difference) |
| Example 1 | 89.01 | 0.52 | 3.54 | 70.05 | 0.87 | 6.26 | 19.15 |
| Example 2 | 90.03 | 0.41 | 2.54 | 69.88 | 0.60 | 6.51 | 20.53 |
| Comparative Example 1 | 93.91 | 0.81 | 2.50 | 69.84 | 0.62 | 8.87 | 24.90 |
| Muscovite | 86.04 | 0.60 | 6.68 | 53.66 | 2.66 | 14.53 | 33.28 |

| Sample | Degree of change of L value | Degree of change of b value |
|---|---|---|
| Example 1 | 18.96 | 2.72 |
| Example 2 | 20.15 | 3.97 |
| Comparative Example 1 | 24.07 | 6.37 |
| Muscovite | 32.38 | 7.85 |

The products of examples 1 and 2 have very little difference of change of the L value (value of brightness) between the wet and dry condition, whereas the product of comparative example 1 (described in JP-A-9-20609) and muscovite have a rather large difference, indicating a lower brightness when wet with oil. A comparison of the b value (degree of yellow) show the same result, where the product of examples 1 and 2 have little degree of change, compared to the product of comparative example 1 and muscovite, which have a large degree of change. This result indicates that the product of comparative example 1 and muscovite, when wet with oil, darken, and make the degree of yellow stronger, indicating larger color drabness. As seen from above, the product of the present invention has remarkably improved color drabness.

[Evaluation of the Gloss by a Spectrophotogoniometer]

The result of the evaluation is shown in FIG. 5, by the method as described above for each sample. From the results, it can be seen that the product of the present invention has a light reflection that is very similar to the skin at all angles, but is a little bit brighter, indicating that such drabness is remarkably improved.

[Visual Evaluation]

Each sample was visually evaluated by the following method. The criterion for evaluation was done in 7 ranks of "not at all", "slightly", "a little", "comparatively", "considerably", "very" and "extremely". The evaluation method of the condition and noticeability of blemishes, was performed as mentioned above.

| Gloss | Not at all 6 points | ~Extremely 0 points |
|---|---|---|
| Noticeability of wrinkles | Not noticeable 6 points | ~Extremely 0 points |
| Transparency | Not at all 0 points | ~Extremely 6 points |
| Noticeability of blemishes | Not noticeable 6 points | ~Extremely 0 points |
| Brightness of skin (Cosmetic film) | Not at all 0 points | ~Extremely 6 points |
| Drabness of skin (Cosmetic film) | Not at all 6 points | ~Extremely 0 points |

[Evaluation of Material]

The result of the evaluation of the material itself for each sample is shown below.

| Sample | Gloss | Noticeability of Wrinkles | Transparency | Noticeability of Blemishes | Brightness of Skin | Drabness of Skin |
|---|---|---|---|---|---|---|
| Example 1 | 5.7 | 5.5 | 5.7 | 5.9 | 5.8 | 5.6 |
| Example 2 | 5.6 | 5.3 | 5.9 | 5.4 | 5.5 | 5.0 |
| Comparative Example 1 | 5.4 | 4.6 | 5.5 | 4.7 | 2.7 | 2.9 |

When the product of the present invention is compared with the product described in JP-A-9-20609, the gloss is kept low, while the transparency is increased, when applied on the skin. It can be seen that the present invention is excellent in its ability to hide the troubled morphology of the skin (make wrinkles less noticeable) and trouble skin tone (make blemishes less noticeable), as well as restraining the drabness, and making the skin look brighter.

[Evaluation of Formulations]

The results of the evaluation of the formulations for each of the samples are shown below.

| Sample | Gloss | Noticeability of Wrinkles | Transparency | Noticeability of Blemishes | Brightness of Skin | Drabness of Skin |
|---|---|---|---|---|---|---|
| Example 5 | 4.5 | 4.9 | 4.6 | 4.9 | 4.9 | 4.7 |
| Example 6 | 4.2 | 4.4 | 4.7 | 4.6 | 4.6 | 4.5 |
| Example 7 | 4.0 | 4.4 | 4.5 | 4.7 | 4.3 | 4.4 |
| Comparative Example 2 | 3.6 | 3.1 | 4.0 | 3.5 | 1.9 | 2.6 |
| Comparative Example 3 | 4.3 | 4.7 | 4.7 | 4.5 | 4.6 | 4.1 |
| Comparative Example 4 | 1.6 | 0.7 | 1.8 | 1.7 | 0.5 | 1.9 |

From the above results, it can be seen that the product of the present invention is remarkably better than the product of the comparative example, with respect to the material itself and the formulation that contains the same. With regard to the present invention, although the material, when included in a formulation, gets diluted by other ingredients, and therefore should have a lower effect than what is expected, is still effective and shows excellent effects when included in a formulation.

Effect of the Invention

When the composite powder in the present invention is included in cosmetics, it shows excellent transparency, makes both the troubled morphology of the skin such as, wrinkles, pore openings, hard texture of the skin less noticeable, and the trouble skin tone of the skin such as, blemishes, freckles, and acne traces less noticeable, as well as having a smoother feel and lesser color drabness, and makes the skin look brighter, when compared to conventional products.

When an aluminum hydroxide layer is covered on the said composite pigment, or a silicone surface treatment is placed on the said composite pigment, the above-defined purpose of the present invention can be increased to an even higher extent.

What is claimed is:

1. A composite pigment comprising a clay mineral and an aluminum hydroxide that adheres to the surface of said clay mineral, wherein said aluminum hydroxide contains an aluminum hydroxide in the form of a cup with cover, the basal plane of which adheres to the surface of said clay mineral.

2. The composite pigment as defined in claim 1, wherein said form of a cup with cover contains a form, where the top surface is somewhat parallel to said cup basal plane, or has a somewhat curved shape, which swells outward to resemble a somewhat muffin-shaped structure.

3. The composite pigment as defined in claim 1, wherein said clay mineral has particles with an average particle size of 0.2~50 µm, or contains particles with a particle size of 0.2~50 µm.

4. The composite pigment as defined in claim 1, wherein said clay mineral has particles with an average thickness of 0.05~1.5 µm, or contains particles with a thickness of 0.05~1.5 µm.

5. The composite pigment as defined in claim 1, wherein the substances in the said form of a cup with cover have an average height range of 0.05~0.5 µm from the top face to its basal plane, or contains ones having a height range of 0.05~0.5 µm from the top face to its basal plane.

6. The composite pigment as defined in claim 1, wherein the structures in said form of a cup with cover, contain ones having a longitudinal cross-sectional shape, without the cover part, of a reverse trapezoid, or a quadrangle, or any shape that resembles these shapes.

7. The composite pigment as defined in claim 1, wherein said aluminum hydroxide that adheres to the surface of said clay mineral is comprised of particles that have an average particle size of 1~80 nm, or includes particles that have a particle size of 1~80 nm.

8. The composite pigment as defined in claim 1, wherein said clay mineral has a refractive index of 1.40~1.80 or includes a clay mineral with a refractive index of 1.40~1.80.

9. The composite pigment as defined in claim 1, wherein said aluminum hydroxide that adheres to said clay mineral exists at a range of 3~75 weight % of the entire weight of the clay mineral to which said aluminum hydroxide adheres including said aluminum hydroxide.

10. The composite pigment as defined in claim 1, further comprising a layer for covering the surface of said aluminum hydroxide.

11. The composite pigment as defined in claim 10, wherein said layer has an average thickness range of 0.001~0.5 µm, or includes one with a thickness range of 0.001~0.5 µm.

12. The composite pigment as defined in claim 1, further comprising a silicone surface treatment layer.

13. The composite pigment as defined in claim 1, wherein said aluminum hydroxide in the said form of a cup with cover exists at at least 30 weight % of the total aluminum hydroxide that adheres to the surface of said clay mineral.

14. The composite pigment as defined in claim 1, wherein said aluminum hydroxide in the said form of a cup with cover exists at at least 30 weight % of the total aluminum hydroxide that adheres to the surface of the clay mineral, adheres in the basal plane of the cup to the surface of said clay mineral, and has an average height, from its cover part to its basal plane, of 0.05~0.5 µm.

15. The composite pigment as defined in claim 1, wherein the basal plane of said aluminum hydroxide that adheres to the surface of said clay mineral, occupies 3~95% of the total surface area of said clay mineral.

16. The composite pigment as defined in claim 10, further comprising a silicone surface treatment layer.

17. Cosmetics, comprising the composite pigment as defined in any one of claims 1–15 and 16 at a usage range of 1–100 weight %.

* * * * *